United States Patent
Schmitt

(10) Patent No.: US 9,488,708 B2
(45) Date of Patent: Nov. 8, 2016

(54) METHOD AND APPARATUS TO GENERATE MAGNETIC RESONANCE ANGIOGRAPHY IMAGES

(75) Inventor: Peter Schmitt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1076 days.

(21) Appl. No.: 13/439,031

(22) Filed: Apr. 4, 2012

(65) Prior Publication Data

US 2012/0271158 A1 Oct. 25, 2012

(30) Foreign Application Priority Data

Apr. 21, 2011 (DE) .......................... 10 2011 007 835

(51) Int. Cl.
| | | |
|---|---|---|
| G01R 33/483 | (2006.01) | |
| A61B 5/00 | (2006.01) | |
| A61B 5/055 | (2006.01) | |
| G01R 33/563 | (2006.01) | |

(52) U.S. Cl.
CPC ........... *G01R 33/4838* (2013.01); *A61B 5/004* (2013.01); *A61B 5/055* (2013.01); *G01R 33/5635* (2013.01)

(58) Field of Classification Search
CPC .. A61B 5/004; A61B 5/055; G01R 33/4838; G01R 33/5635
See application file for complete search history.

(56) References Cited

U.S. PATENT DOCUMENTS

| 5,786,693 A | 7/1998 | Gullapalli et al. |
| 5,842,989 A * | 12/1998 | Zur ............................. 600/410 |
| 2005/0215881 A1 | 9/2005 | Van Zijl et al. |
| 2009/0010513 A1 | 1/2009 | Kirsch |
| 2009/0093703 A1 | 4/2009 | Silber |
| 2010/0280357 A1 | 11/2010 | Bi et al. |
| 2012/0016224 A1 | 1/2012 | Schmitt |

FOREIGN PATENT DOCUMENTS

| JP | H07308302 A | 11/1995 |
| JP | 2004008516 A | 1/2004 |

* cited by examiner

*Primary Examiner* — Katherine Fernandez
(74) *Attorney, Agent, or Firm* — Schiff Hardin LLP

(57) ABSTRACT

In a magnetic (MR) method and apparatus to generate an MR angiography image of a vascular structure of an examination region, spins in the examination region are saturated by an RF saturation pulse to cause these spins to produce a lower signal intensity in the angiography image than spins that flow from a major artery via a feed artery into the examination region, which are not saturated by the RF saturation pulse. A saturation volume is established that is saturated by the RF saturation pulse in order to be able to depict substantially all the vascular structure, such that the major artery and the tissue surrounding the major artery are not situated at the level of the branching of the feed artery in the saturation volume. The MR angiography image is generated using the established saturation volume.

5 Claims, 3 Drawing Sheets

METHOD AND APPARATUS TO GENERATE MAGNETIC RESONANCE ANGIOGRAPHY IMAGES

BACKGROUND OF THE INVENTION

1. Field of the Invention

The present invention concerns a method to generate a magnetic resonance angiography image of a vascular structure of an examination region, and MR system for implementing such a method.

2. Description of the Prior Art

For the depiction of vessels with magnetic resonance tomography (MRT), methods are used in which contrast agent is injected into an examined person, the propagation of which contrast agent in the body then being detected. Furthermore, angiography techniques implemented without contrast agent are known in which the influence of flowing spins on the MR signal is used. In this angiography technique operating without contrast agent, a technique known as spin labeling (i.e. a marking of the spins) is used, among other things. A slice-shaped volume that includes the vessels to be depicted is hereby marked with the use of a slice-selective saturation pulse. This volume forms the saturation volume that is excited by radiation of one or more RF saturation pulses.

The term "saturation pulse" is generically used in the following as a designation for pulses that are used to magnetically mark the saturation volume. They can be (but do not necessarily need to be) pulses with an excitation angle of 90 degrees which, in combination with what are known as spoiler gradients, lead directly to a saturation of the volume. The term "saturation pulse" also encompasses other types of pulses that (for example) lead to a saturation of the magnetization at later points in time, such as inversion pulses with a target flip angle of 180 degrees, for example.

After excitation of the spins in the saturation volumes, the spins are detected after an inversion time period TI, with the inversion time period being selected such that the inverted spins ideally contribute no signals to the total signal in the signal acquisition. In comparison to the saturated spins, the spins flowing from outside the saturation volume into the volume via the feed (supply or delivery) vessels have a high signal strength in the signal acquisition, which is then used to generate the MR angiography image.

However, in the case of examined persons with a low cardiac output, or in regions with slow blood flow, it is difficult to sufficiently fill the vessel tree of interest with fresh, unsaturated, inflowing blood, particularly if the inversion time period is short. Those portions of the vessel tree that are not reached by the fresh, unsaturated spins remain dark in the arising MR angiography image. Due to the preceding inversion, the blood that flows from the saturation volume into the vessel tree generates nearly no signal, and therefore shortens the length of the portion of the vessel tree that is visible within the MR angiography images.

In order to ensure the visibility of optimally the entire vessel tree, up to the peripheral branchings of the vessel structure, even for patients with a low cardiac output, it is sought to place the interface between the saturated volume and the unsaturated volume as close as possible to the vessel tree to be examined.

SUMMARY OF THE INVENTION

An object of the present invention to improve the quality of MR angiography images, particularly for patients with low cardiac output.

According to a first aspect of the present invention, a method is provided to generate an MR angiography image of a vascular structure of an examination region in which spins in the examination region are saturated by radiation of at least one RF saturation pulse, and in which these spins have a lower signal intensity in the subsequent MR signal acquisition for the generation of the MR angiography image, compared to spins that flow from a major artery via a feed artery into the examination region and are not saturated by the at least one RF saturation pulse, and that thus have a significantly increased signal intensity relative to the saturation spins. According to this aspect of the invention, the saturation volume is established by radiation of the at least one RF saturation pulse in order to be able to depict the vascular structure in the examination region. According to the present invention, the saturation volume is established such that the major artery and the tissue surrounding the major artery are not situated at the level of the branching of the feed artery in the saturation volume. The MR angiography image can then subsequently be generated with the use of the established saturation volume. A basis of the present invention is the recognition that the tissue around the major artery at the level of the branching of the feed artery does not necessarily have interfering signal portions if it is not saturated. Therefore, it is possible to except this region around the major artery from the saturation. This means that the proportion of the flowing spins that were not saturated by the saturation pulse can be placed closer to the actually interesting vascular structure. The signal proportions of the spins that flow unsaturated into the examination region can thereby be increased, which is reflected in an improved signal intensity in the vessels of the vascular structure to be depicted. According to the invention, the visibility of the vessel tree is thereby increased up to the peripheral branchings, even given patients with low cardiac output. It has been recognized that the segment of the vascular structure that is located at the level of the branching of the feed artery does not need to be contained in the saturation volume, since the surrounding tissue provides no significantly bright signal portion in the actual signal acquisition for the generation of the MR angiography image, even without saturation.

In a further embodiment, before establishing the saturation volume it is possible to check whether a tissue that surrounds the major artery at a level of a branching of the feed artery would have a significantly increased signal intensity in the MR angiography image relative to the saturated spins. If this is not the case, this region can be spared from the saturation volume as described. This means that, in this embodiment, before the final establishment of the saturation volume a check is made as to whether a saturation of the tissue at the level of the branching of the feed artery is actually necessary or not. If it is deemed to be necessary, the surrounding tissue should be included in the saturation volume. If this is not the case, i.e. if the tissue surrounding the major artery, when unsaturated, delivers no significantly higher signal contribution than the saturated spins otherwise situated in the examination region, a saturation of this tissue surrounding the major artery is not necessary.

In a further embodiment, within the examination region it is also possible to identify a signal tissue that would have a strongly increased signal intensity in the MR angiography image relative to the saturated spins if it were not situated in the saturation volume. The saturation volume is then established such that said saturation volume is limited essentially to a region surrounding this signal tissue. As used herein, "signal tissue" means the tissue within the examination region that, if it were not saturated, would have an interfering, high signal proportion in the acquisition of the MR angiography image. If it is not saturated, the signal tissue would deliver a high signal in the MR angiography image, similar to the blood vessels, whereby the visibility of the actual vessels in the MR angiography image would be negatively affected. In this type of MR angiography technique, all spins except for the spins in the blood vessels should have a low signal in the signal acquisition so that a good contrast between bright vessels and dark background signal is achieved in the signal acquisition.

In a further embodiment it is possible to assemble the saturation volume from two separate partial saturation volumes. These two separate partial saturation volumes can now be placed so that the major artery and the tissue surrounding the major artery are not situated at the level of the branch in the saturation volume.

One possibility for application of the present invention is in the generation of MR angiography images of the two kidneys. It is hereby not necessary to include the aorta at the level of the branching of the respective renal arteries in the saturation volume. The proportion of unsaturated spins in proximity to the renal arteries is thereby increased, such that overall the depiction of the vascular structure is improved since unsaturated blood can also penetrate into the smaller renal arteries until the switching of the next saturation pulse. Given the application of the invention for the generation of MR angiography images of the kidneys, two separate partial saturation volumes can now also be selected such that two oblique partial saturation volumes are selected that cover the kidneys themselves, but not the aorta at the level of the branching of the respective renal arteries. Furthermore, the two partial saturation volumes can be selected such that the heart is included in neither of the two partial saturation volumes. A saturation of the spins within the heart should advantageously be avoided since otherwise the spins flowing into the aorta would already be saturated before they flow into the saturation region.

In another embodiment, it is furthermore possible to limit the saturation volume to essentially only the volume that includes both kidneys in the examination region. This means that the saturation volume can be specifically limited to the volume in the examination region that includes both kidneys in the examination region.

For example, 2-dimensional or 3-dimensional, spatially selective inversion pulses can be used to saturate the spins within the saturation volume. With these spatially selective inversion pulses it is possible to invert the spins (and therefore saturate them) only in spatially delimited target volumes. The use of 2- or 3-dimensional, spatially selective inversion pulses can also be combined with parallel transmission techniques given the use of multiple transmission channels. Given the use of parallel transmission techniques with multiple channels, the selection of spatially delimited saturation volumes can be further improved.

Furthermore, it is possible to automatically identify the examination region via image post-processing techniques, wherein the saturation volume is automatically determined depending on the identified examination region. For example, if the examination region is identified with the use of the image post-processing technique as the region of the kidneys, the system can be designed such that the information is stored that the aorta in the region of the branching of the renal arteries does not need to be saturated, such that the saturation volume can be automatically matched to this.

To calculate the two-dimensional or three-dimensional, spatially selective inversion pulse, it is possible to base this on a calculation excitation field of view or excitation k-space that is selected such that the corresponding dimension of the saturation volume in the examination subject covers only one or the two partial saturation volumes, and an edge of the saturation volume situated in the middle between the two partial saturation volumes. The saturation pulses thus can be designed to be of a shorter duration.

Furthermore, it is possible for the check as to whether the surrounding tissue is interfering is to implement an MR measurement that essentially corresponds to the angiography measurement with regard to the time lapse and the design of the imaging sequences, wherein the spatial resolution is reduced, however, or a two-dimensional measurement is implemented instead of a three-dimensional measurement. This pre-measurement is advantageously selected such that it can be acquired in a time period of between 20 seconds and 30 seconds. One example is a known 2D Trufi sequence with an inversion pulse.

The invention furthermore concerns an MR system to acquire an MR angiography image as described above, with an RF control unit to radiate the at least one RF saturation pulse and a unit to calculate the saturation pulse, wherein this unit establishes the saturation volume such that the major artery and the tissue surrounding the major artery are not situated at the level of the branching of the feed artery in the saturation volume.

Furthermore, an MR image acquisition unit is provided that acquires the MR angiography image using the determined saturation volume.

DESCRIPTION OF THE PREFERRED EMBODIMENTS

Figure 1:
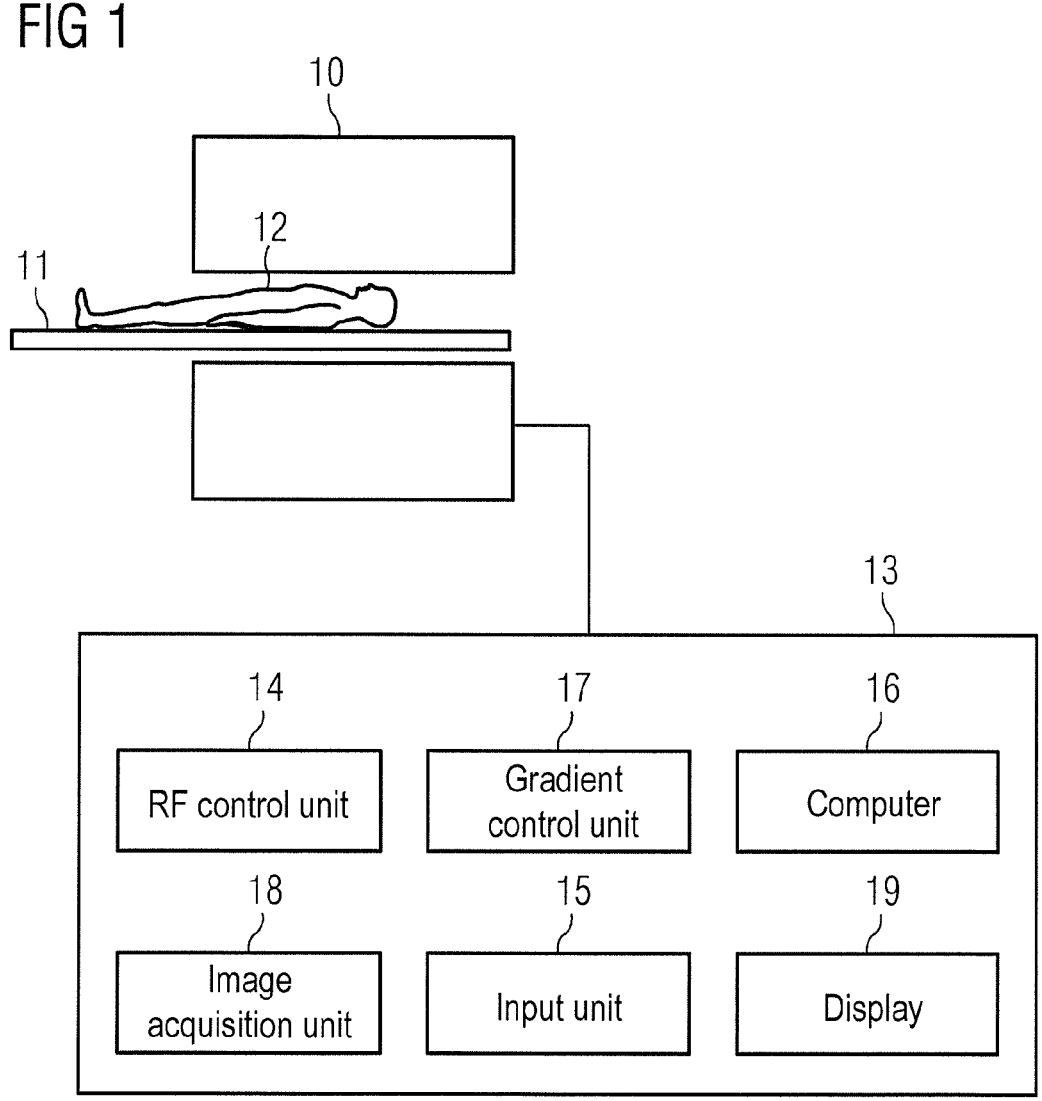
FIG. 1 schematically shows an MR system with which an MR angiography image with improved depiction of the vascular structure can be acquired.

In FIG. 1 an MR system is schematically shown with which an MR angiography image with improved depiction of the vascular structure can be acquired. The MR system has a magnet 10 to generate a polarization field $B_0$. An examined person 12 arranged on a bed 11 is slid into the magnet 10, wherein the magnetization resulting in the examined person is flipped out of the steady state via radiation of radio-frequency pulses, wherein the relegation process occurring after radiation of the RF pulses is detected with coils (not shown). For spatial coding of the detected signals, magnetic field gradients are furthermore applied via gradient coils in order to achieve a spatial dependency of the detected resonance frequency. The arrangement of the magnet 10 with the gradient coils and RF coils therein is commonly called an MR scanner The general method of how signals can be generated and read out via a sequence of radiated RF pulses and the switching of magnetic field gradients is known to the man skilled in the art and need not be explained in detail herein.

The MR system furthermore has a central control unit 13 with which the MR system is controlled. The central control unit has an RF control unit 14 to control the radiated RF pulses. Furthermore, an operating unit is provided with which a user can graphically determine the saturation volume that should be saturated via radiation of the at least one RF saturation pulse. Furthermore, a unit to calculate the saturation volume is provided that, using the graphical definition, determines the saturation volume that is saturated via radiation of the at least one RF saturation pulse for the depiction of the vascular structure. The input unit is shown with reference character 15 in FIG. 1. The unit to calculate the saturation pulse is generally designated as computer 16. The central control unit 13 furthermore has a gradient control unit 17 to control the switching of the magnetic field gradients. An image acquisition unit 18 controls the workflow of the radiated RF pulses and the employed gradients depending on the selected imaging sequence. This means that the image acquisition unit controls the RF control unit 14 and the gradient control unit 17, among other things. After detection of the MR signals via coils (not shown), the MR signals can be converted into MR images and displayed at a display 19 (as is generally known).

As is explained in detail in connection with FIG. 2 through 5, the MR system shown in FIG. 1 is in the position to depict vascular structures in detail in an MR angiography measurement, even in examined persons with low cardiac output.

Figure 3:
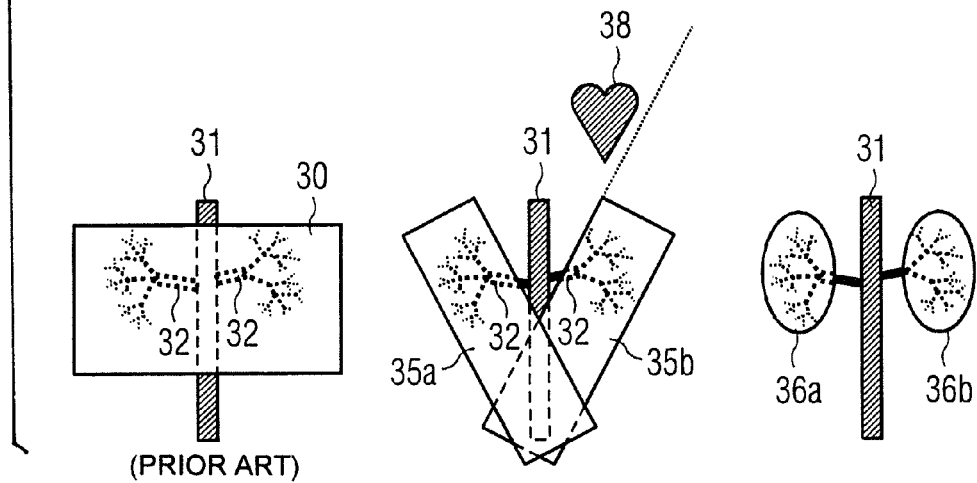
FIG. 3 schematically shows the position of saturation volumes according to the prior art and according to the invention.

In the angiography technique that is used here, the spins arranged in an examination region are saturated via radiation of at least one RF saturation pulse. The saturation volume is hereby typically selected by a user of the MR system. In FIG. 3 a saturation volume 30 is schematically shown that was selected by an operator according to the prior art in order to implement an MR angiography measurement of both kidneys. The saturation volume 30 can hereby be placed by an operator in previously generated overview images. In the embodiment according to the prior art that is shown in the left image of FIG. 3, a majority of the spins in the aorta 31 were also concurrently saturated, like the spins in the two renal arteries 32.

Embodiments of the invention are now shown in the middle Figure of FIG. 3 and the right Figure of FIG. 3. As is apparent in the middle image of FIG. 3, the conventional saturation volume is replaced in accordance with the invention with two separate partial saturation volumes 35*a* and 35*b* that still saturate the tissue in the kidneys. However, it is to be noted that the aorta up to the branching of the renal arteries is not included in the saturation volume. The entire renal artery is similarly not included in the saturation volume 35*a* nor in the saturation volume 35*b*. In the examples shown in the middle in FIG. 3, two obliquely overlapping partial saturation volumes 35*a* and 35*b* are selected. The choice of the middle partial saturation volumes 35*a* and 35*b* as compared to the saturation volume 30 is based on the realization that the tissue that surrounds the aorta is not signal tissue at the level of the outlets of the renal arteries, i.e. is not tissue that—if it were not saturated—would contribute to high signal intensities in the acquisition of the signals for the MR angiography.

Figure 2:
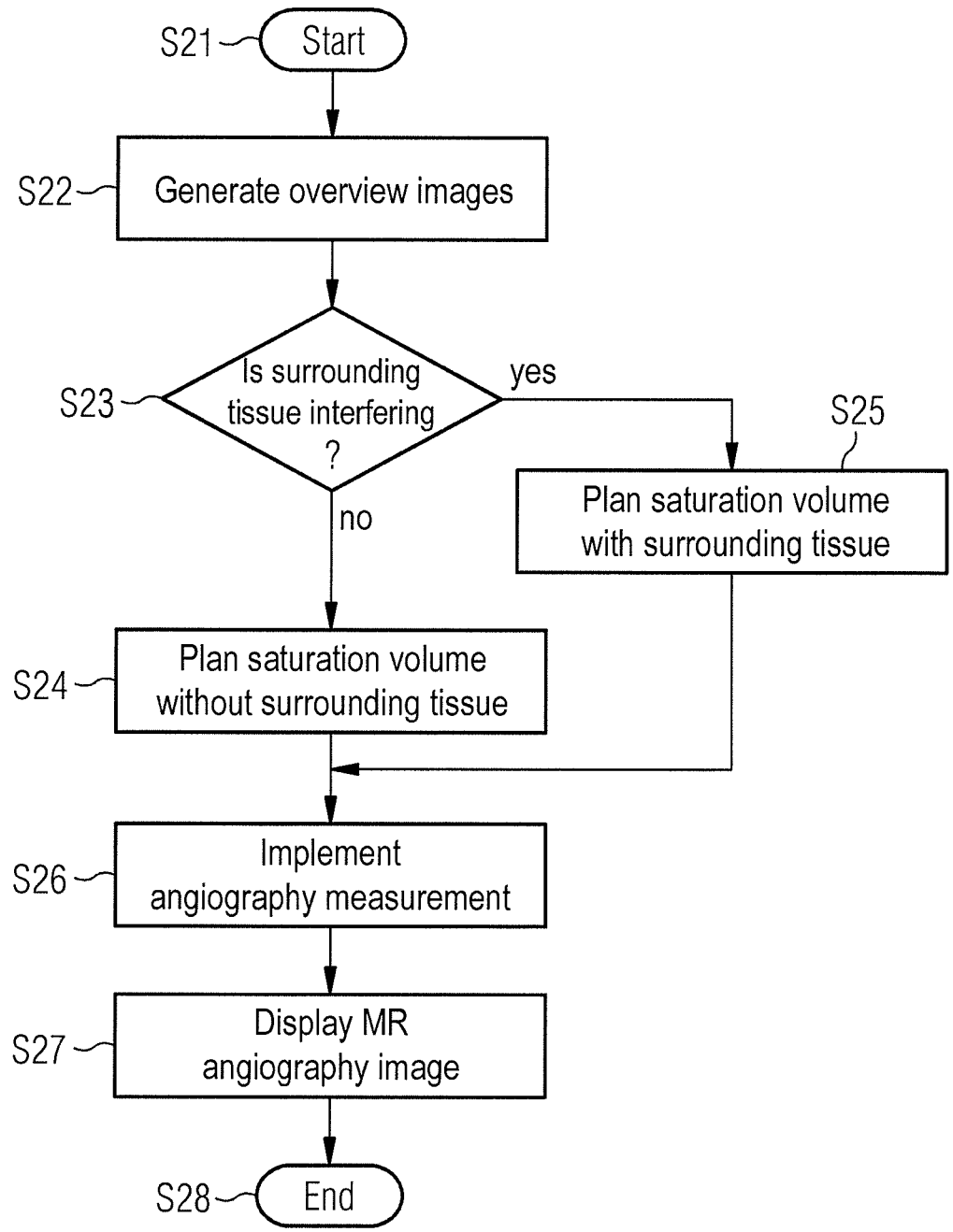
FIG. 2 is a flowchart of the basic steps to generate an MR angiography image according to the present invention.

With regard to FIG. 2, the method proceeds as follows. The methods starts at Step S21, and in Step S22 overview images are generated at which the saturation volume or volumes can be drawn, for example with the aid of an operating unit 16. In the selection of the saturation volume it is checked in Step S23 whether the surrounding tissue is signal tissue or not. If it is detected in Step S23 that the tissue around the vessels does not have any interfering signal portions in the acquisition of the MR angiography if it is not saturated, in Step S24 the saturation volume can be planned such that the surrounding tissue is not included in the saturation volume. However, if it is detected in Step S23 that the surrounding tissue is signal tissue and therefore would interfere in the MR angiography image without saturation, in Step S25 the planning of the saturation volume takes place such that the signal tissue identified as interfering is included in the saturation volume.

In a further Step S26, the angiography measurement can then be implemented with the use of the saturation volume established in Step S24 or S25. The angiography measurement itself corresponds to the known angiography measurement in which the difference in the signal intensity between saturated and unsaturated spins is used to show the vessels. The MR signals acquired in Step S26 can ultimately be presented in a calculated MR angiography image in Step S26 before the method ends in Step S28.

Referring in turn to FIG. 3, this means that in Step S23 it was established that the tissue around the aorta that is present at the level of the renal arteries is not signal tissue and therefore does not need to be saturated, such that this region can be excepted from the saturation. By comparing the saturation volumes in the left image and middle image of FIG. 3, it is apparent that a larger region in proximity to the kidneys has unsaturated spins in the middle image of FIG. 3. The path of the unsaturated spins in the smaller branches of the arteries is shorter than in the exemplary embodiment that is shown to the left in FIG. 3. This means that a higher signal difference relative to the saturated volume can be achieved, even for the smaller arteries.

In the embodiment shown in the middle example, in the selection of the two partial saturation volumes 35*a* and 35*b* it should be heeded that the heart 38 is not included in the saturation volume 35*b*.

Furthermore, in the right example of FIG. 3 a saturation with two partial saturation volumes 36*a* and 36*b* according to the invention is shown. Since it has been recognized that the tissue surrounding the aorta does not need to be saturated, the saturation volume can be limited to the kidney tissue itself. As is apparent via comparison of the right exemplary embodiment and middle exemplary embodiment, given the selection of the partial saturation volumes 36*a* and 36*b* the proportion of unsaturated spins is additionally increased precisely in the area of the kidneys, thereby additionally improving the generated MR angiography images. In the right example shown in FIG. 3, it is not a slice-shaped volume (such as the volume 30 to the left in FIG. 3, for example) that is saturated; rather, a customized volume is saturated. The saturation of such a delimited spatial volume is possible via the use of 2- or 3-dimensional, spatially selective inversion pulses. By means of a Fourier analysis or advanced calculation method, a temporally varying-gradient curve and an associated RF pulse progression for the saturation pulse can be calculated based on the specific volume, which saturation pulse is then used to saturate or invert the specific volume (such as the volume 36*a* and 36*b*). The underlying approach here has a certain analogy to the generation of an MR image in which k-space is scanned by the application of temporally varying magnetic field gradients. The switching of a long RF pulse or multiple short, successive RF pulses represents a weighting along this trajectory. The resulting excitation profile—i.e.

the specific saturation volume—results from the Fourier transformation of this weighted excitation k-space. The necessary RF and gradient curves can be generated from the desired excitation profile by means of a Fourier analysis or advanced calculation method. Various trajectory courses are conceivable in order to cover and scan excitation k-space. With regard to the two partial saturation volumes 36a and 36b, this means that elliptically shaped volumes must be saturated, whereby a suitable excitation k-space must be filled. This means that this excitation k-space must be traversed by the trajectory during the excitation pulse, wherein in the trajectory RF energy must be deposited in a pattern that leads to the desired saturation volume. The excitation field must typically be selected large enough in order to avoid an unwanted repetition of the excitation in the examination subject (i.e. the human body). The size of the excitation field—i.e. the area via which regions that are not to be excited are also unambiguously defined—reciprocally coincides with the spacing of the dots traversing excitation k-space. This means that the trajectory through excitation k-space must normally be sufficiently dense for a clear delimitation of a saturation volume.

Figure 4:
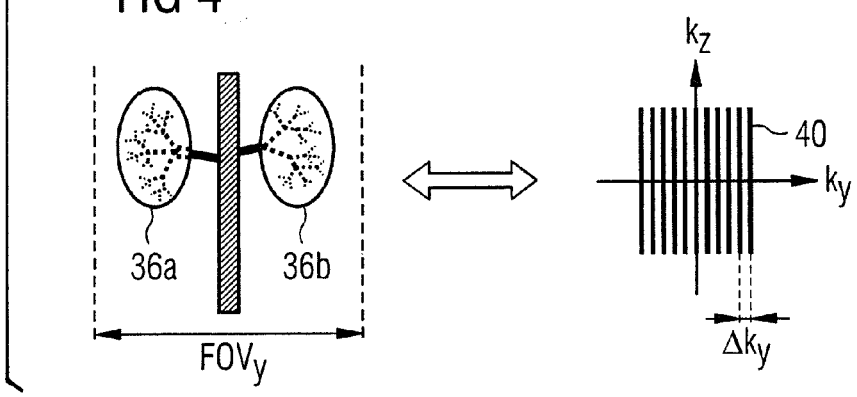
FIG. 4 shows an exemplary embodiment with the schematic position of two spatially delimited partial saturation volumes.
Figure 5:
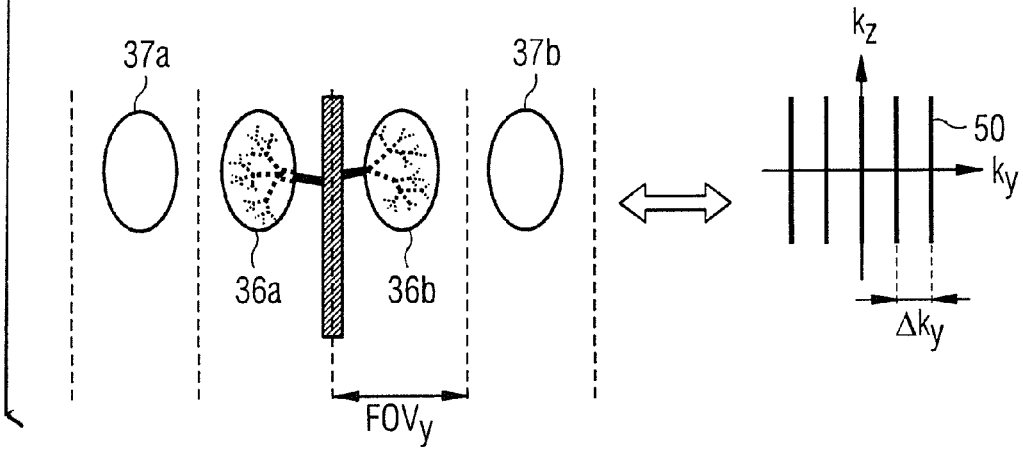
FIG. 5 shows an additional example with the position of two spatially delimited saturation volumes in the kidneys.

In FIG. 4 a trajectory 40 in excitation k-space is shown in the right image of FIG. 4 would actually be necessary for the saturation in the two partial saturation volumes 36a and 36b. The larger the excitation field $FOV_y$ that is selected, the smaller the corresponding distance $\Delta k_y$ of the required excitation k-space that must be selected. The excitation pattern within the excitation field repeats periodically outside of the FOV, but this is not shown in FIG. 4. Due to the fact that two identical geometries should be saturated, and due to the fact that critical tissue whose saturation can be interfering is no longer present within a radial distance outside of the partial saturation volumes, an excitation trajectory as shown in FIG. 5 can also be used. This means that a reduced excitation field of view can be used as depicted by the trajectory 50 through the less dense scanning of excitation k-space. The excitation field of view entering into the calculation is thereby selected so that it is as wide as the separation of the two partial saturation volumes, and so that an edge comes to lie precisely in the middle between the two partial saturation volumes. For example, the partial saturation volume 36b directly results as a continuation of the partial saturation volume 36a. Additional further partial saturation volumes 37a and 37b do in fact result. However, these partial saturation volumes 37a and 37b are not interfering in the MR angiography imaging since no blood that contemporaneously flows into the target volume and whose saturation would lead to unwanted effects is located in the partial saturation volumes 37a and 37b. Due to the less dense scanning of excitation k-space, it is possible to generate the necessary RF pulses to generate a saturation pattern as shown in FIG. 5. The RF pulses can thereby be designed with a shorter duration, which can be advantageous. Alternatively, the obtained time can be used in order to extend excitation k-space further outward than in the exemplary embodiment of FIG. 4, such that sharper edges are possible between saturated volumes and unsaturated volumes.

The steps implemented in Step S23 and S24 can be implemented by an operator of the MR system or automatically. Given automatic implementation of these steps, the anatomy shown in the overview images is identified via image post-processing techniques and, on the basis of the identified anatomy, it is automatically determined how the saturation volume must be placed, meaning that information as to whether tissue types that are not signal tissue are possibly present in the examination region is stored in the system, such that these tissue regions could be excluded from the saturation volumes.

In summary, the present invention enables the generation of MR angiography images in which the proportion of unsaturated blood that flows into the examination region can be increased.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate a magnetic resonance (MR) angiographic image of a vascular structure in a subject, comprising:

operating an MR scanner from a control computer to execute with a pulse sequence to acquire MR data from the subject in a form allowing said angiographic image of an examination region of the subject that encompasses said vascular structure to be reconstructed, said vascular structure comprising branches fed by a feed artery that is in turn fed by a major artery, said branches branching from said feed artery at a branching location, wherein operating the MR scanner to acquire the MR data comprises:

in said control computer, controlling said pulse sequence to radiate at least one radio-frequency (RF) saturation pulse into the subject that saturates nuclear spins in a saturation volume in the subject to produce saturated spins in said saturation volume that exhibit a lower signal intensity in said angiographic image than non-saturated nuclear spins;

in said control computer, determining, from an acquired preliminary image of the subject, a signal intensity of said tissue that surrounds said major artery that is expected to occur in the angiographic image that is to be reconstructed; and in said control computer, configuring said at least one RF saturation pulse that is radiated in said pulse sequence to give said saturation volume in said subject a shape that includes said vascular structure in said saturation volume but that excludes said major artery and said feed artery from said saturation volume, and that selectively excludes tissue that surrounds said major artery before said branching location from said saturation volume dependent on said determined signal intensity of said tissue that surrounds said major artery; and in an image reconstruction computer, reconstructing said angiographic image from said MR data in which said vascular structure is substantially completely depicted by virtue of non-saturated nuclear spins flowing into said vascular structure from said main artery and said feed artery, due to the saturation volume defined by configuring said at least one RF saturation pulse, and making the reconstructed angiographic image available from the reconstruction computer in electronic form.

2. A method as claimed in claim 1, wherein determining said signal intensity comprises determining whether nuclear spins in said tissue that surrounds said major artery before said branching location would have a substantially increased signal intensity in said reconstructed angiographic image with respect to said lower signal intensity of said saturated spins if said nuclear spins in said tissue surrounding said major artery were not saturated, and configuring said at least one RF saturation pulse to define said saturation volume in said subject so as to include said tissue surrounding said major artery in said saturation volume only if said tissue that surrounds said major artery would produce said substantially increased signal intensity in said reconstructed angiography image if said nuclear spins in said tissue that surrounds said major artery were not saturated.

3. An apparatus to generate a magnetic resonance (MR) angiographic image of a vascular structure in a subject, comprising:

an MR scanner;

a control computer configured to operate said MR scanner with a pulse sequence to acquire MR data from the subject in a form allowing said angiographic image of an examination region of the subject that encompasses said vascular structure to be reconstructed, said vascular structure comprising branches fed by a feed artery that is in turn fed by a major artery, said branches branching from said feed artery at a branching location, wherein said control computer is configured to operate said MR scanner to acquire the MR data by:

controlling said pulse sequence to radiate at least one radio-frequency (RF) saturation pulse into the subject that saturates nuclear spins in a saturation volume in the subject to produce saturated spins in said saturation volume that exhibit a lower signal intensity in said angiographic image than non-saturated nuclear spins;

determining, from an acquired preliminary image of the subject, a signal intensity of said tissue that surrounds said major artery that is expected to occur in the angiographic image that is to be reconstructed; and operating said MR scanner to radiate said at least one RF saturation pulse in said pulse sequence in a form that gives said saturation volume in said subject a shape that includes said vascular structure in said saturation volume but that selectively excludes said tissue that surrounds said major artery before said branching location from said saturation volume dependent on said determined signal intensity of said tissue that surrounds said major artery; and a reconstruction computer configured to reconstruct said angiographic image from said MR data in which said vascular structure is substantially completely depicted by virtue of non-saturated nuclear spins flowing into said vascular structure from said main artery and said feed artery, due to the saturation volume defined by said at least one RF saturation pulse, and to make the reconstructed angiographic image available from the reconstruction computer in electronic form.

4. An apparatus as claimed in claim 3, wherein said control computer is configured when determining said signal intensity, to determine whether nuclear spins in tissue that surrounds said major artery before said branching location would have a substantially increased signal intensity in said reconstructed angiographic image with respect to said lower signal intensity of said saturated spins if said nuclear spins in said tissue surrounding said major artery were not saturated, and to configure said at least one RF saturation pulse to define said saturation volume in said subject so as to include said tissue surrounding said major artery in said saturation volume only if said tissue that surrounds said major artery would produce said substantially increased signal intensity in said reconstructed angiography image if said nuclear spins in said tissue that surrounds said major artery were not saturated.

5. An apparatus as claimed in claim 4 wherein said control computer is configured to determine whether said tissue that surrounds said major artery would produce said substantially increased signal intensity in said reconstructed angiographic image if the nuclear spins therein were not saturated by operating said MR scanner with said subject therein to acquire said preliminary image with a further pulse sequence comparable to said pulse sequence used to acquire said MR data for said angiographic image but with at least one of a reduced spatial resolution and reduced size of said examination volume with respect to said pulse sequence to acquire said MR data for said angiographic image.

* * * * *